US00PP22895P2

(12) United States Plant Patent
Oudolf

(10) Patent No.: US PP22,895 P2
(45) Date of Patent: Jul. 24, 2012

(54) ***SCABIOSA* PLANT NAMED 'CHAMPAGNE'**

(50) Latin Name: *Scabiosa ochroleuca*
Varietal Denomination: Champagne

(75) Inventor: Petrus Hendricus Oudolf, Hummelo (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 12/931,677

(22) Filed: Feb. 7, 2011

(51) Int. Cl.
*A01H 5/00* (2006.01)

(52) U.S. Cl. ..... Plt./478

(58) Field of Classification Search ..... Plt./478
See application file for complete search history.

*Primary Examiner* — Annette Para
(74) *Attorney, Agent, or Firm* — C. A. Whealy

(57) ABSTRACT

A new and distinct cultivar of *Scabiosa* plant named 'Champagne', characterized by its upright and somewhat outwardly spreading plant habit; long flowering period; large involucrate heads with numerous light purple-colored flowers; and good garden performance.

2 Drawing Sheets

Botanical designation: *Scabiosa ochroleuca.*
Cultivar denomination: 'CHAMPAGNE'.

BACKGROUND OF THE INVENTION

The present invention relates to a new and distinct cultivar of *Scabiosa* plant, botanically known as *Scabiosa ochroleuca* and hereinafter referred to by the name 'Champagne'.

The new *Scabiosa* plant originated from an open-pollination during the summer of 2001 in Hummelo, The Netherlands, of an unnamed selection of *Scabiosa ochroleuca*, not patented, as the female, or seed, parent with an unknown selection of *Scabiosa ochroleuca* as the male, or pollen, parent. The new *Scabiosa* plant was discovered and selected by the Inventor as a single flowering plant from within the progeny of the stated open-pollination in a controlled environment in Hummelo, The Netherlands during the summer of 2002.

Asexual reproduction of the new *Scabiosa* plant by softwood cuttings in a controlled environment in Hummelo, The Netherlands since the summer of 2002, has shown that the unique features of this new *Scabiosa* plant are stable and reproduced true to type in successive generations.

SUMMARY OF THE INVENTION

Plants of the new *Scabiosa* have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'Champagne'. These characteristics in combination distinguish 'Champagne' as a new and distinct *Scabiosa* plant:

1. Upright and somewhat outwardly spreading plant habit.
2. Long flowering period.
3. Large involucrate heads with numerous light purple-colored flowers.
4. Good garden performance.

Plants of the new *Scabiosa* differ from plants of the female parent selection primarily in flower color as plants of the new *Scabiosa* have lighter-colored flowers than plants of the female parent selection. In addition, plants of the new *Scabiosa* flower for a longer period of time than plants of the female parent selection.

Plants of the new *Scabiosa* can be compared to plants of *Scabiosa columbaria* 'Pink Mist', disclosed in U.S. Plant Pat. No. 8,957. Plants of the new *Scabiosa* differ primarily from plants of 'Pink Mist' in flower color as plants of 'Pink Mist' have pink-colored flowers. In addition, plants of the new *Scabiosa* flower for a longer period of time than plants of 'Pink Mist'.

BRIEF DESCRIPTION OF THE PHOTOGRAPHS

The accompanying colored photographs illustrate the unique appearance of the new *Scabiosa* plant showing the colors as true as it is reasonably possible to obtain in colored reproductions of this type. Colors in the photographs may differ from the color values cited in the detailed botanical description which accurately describe the colors of the new *Scabiosa* plant.

The photograph at the top of the first sheet comprises a side perspective view of typical flowering plants of 'Champagne' grown in ground beds.

The photograph at the bottom of the first sheet is a close-up view of the upper surface of a typical leaf of 'Champagne'.

The photograph on the second sheet is a close-up view of a typical inflorescence of 'Champagne'.

DETAILED BOTANICAL DESCRIPTION

The aforementioned photographs and following observations, measurements and values describe plants grown during the late summer in ground beds in an outdoor nursery in Rijpwetering, The Netherlands and under typical production conditions. During the production of the plants, day temperatures ranged from 12° C. to 32° C. and night temperatures ranged from 6° C. to 16° C. Plants were one year old when the photographs and the description were taken. In the detailed description, color references are made to The Royal Horticultural Society Colour Chart, 2007 Edition, except where general terms of ordinary dictionary significance are used.

Botanical description: *Scabiosa ochroleuca* 'Champagne'.

Parentage:

*Female, or seed, parent*.—Unnamed selection of *Scabiosa ochroleuca*, not patented.

*Male, or pollen, parent*.—Unknown selection of *Scabiosa ochroleuca*, not patented.

Propagation:

*Type*.—Softwood cuttings.

*Time to initiate roots, summer*.—About four weeks at 18° C.

*Time to produce a rooted young plant*.—About three months at 18° C.

*Root description*.—Fine, fibrous; creamy white in color.

*Rooting habit*.—Freely branching; medium density.

Plant description:

*Plant and growth habit*.—Herbaceous perennial; upright and somewhat outwardly spreading; inverted triangle; open, airy appearance; flowers arranged in involucrate heads held above the foliar plane on long peduncles; low vigor.

*Plant height*.—About 39 cm.

*Plant spread*.—About 27.8 cm.

*Lateral branch description*.—Length: About 2 cm. Diameter: About 2 mm. Internode length: About 2 cm. Texture: Sparsely pubescent. Color: Close to 138A to 138B; just above the nodes, slightly tinged with close to N186C.

Foliage description:

*Arrangement*.—Opposite, simple.

*Length*.—About 4.4 cm.

*Width*.—About 3.3 cm.

*Shape*.—Ovate.

*Apex*.—Acute.

*Base*.—Cuneate.

*Margin*.—Pinnatisect.

*Texture, upper and lower surfaces*.—Smooth, glabrous.

*Venation pattern*.—Pinnate.

*Color*.—Developing leaves, upper surface: Close to 137A. Developing leaves, lower surface: Close to 137B. Fully expanded leaves, upper surface: Close to 137A; venation, close to 138A. Fully expanded leaves, lower surface: Close to 137B to 137C; venation, close to 137B to 137C.

*Petioles*.—Length: About 3 mm. Diameter: About 1 mm. Texture, upper and lower surfaces: Smooth, glabrous. Color, upper and lower surfaces: Close to 137B to 137C.

Inflorescence description:

*Appearance*.—Flowers arranged in terminal involucrate heads displayed above the foliar plane on long peduncles; flowers face upright to slightly outwardly.

*Fragrance*.—None detected.

*Time to flowering and flowering period*.—Plants begin flowering about nine months after planting; long flowering period, in the garden, plants flower continuously during August and September in The Netherlands.

*Inflorescence longevity*.—Flowers typically last about one week on the plant; flowers not persistent.

*Fragrance*.—None detected.

*Inflorescence diameter*.—About 3.2 cm.

*Inflorescence height*.—About 1.4 cm.

*Inflorescence buds*.—Length: About 4 mm. Diameter: About 2 mm. Shape: Obovate. Color: Close to 145A; towards the base, 145C to 145D.

*Outer flowers*.—Quantity per inflorescence: About twelve. Diameter: About 1.3 cm. Length: About 1.5 cm. Petals: Quantity per flower: Five in a single whorl, lower 25% of the petals are fused. Length: Larger lower three petals, about 1.5 cm; smaller upper two petals, about 1 cm. Width: Lower three petals, about 4 mm; upper two petals, about 2 mm. Shape: Spatulate. Apex: Rounded. Margin: Entire. Texture, upper and lower surfaces: Smooth, glabrous; inside the tube, densely pubescent. Color: When opening, lower three petals, upper surface: Close to 75B to 75C; towards the base, tinged with close to 157B. When opening, lower three petals, lower surface: Close to 75C; towards the base, tinged with close to 157B. When opening, upper two petals, upper and lower surfaces: Close to 75D. Fully opened, lower three petals, upper and lower surfaces: Close to 75C; towards the base, tinged with close to 157B. Fully opened, upper two petals, upper and lower surfaces: Close to 75D.

*Central flowers*.—Quantity per inflorescence: About 38. Diameter: About 3 mm. Length: About 1 cm. Petals: Quantity per flower: Five in a single whorl, lower 85% of the petals are fused. Length: About 1 cm. Width: About 1.5 mm. Shape: Oblanceolate. Apex: Rounded. Margin: Entire. Texture, upper and lower surfaces: Smooth, glabrous; inside the tube, densely pubescent. Color: When opening, upper and lower surfaces: Close to 75D; towards the apex, close to 157D. Fully opened, upper and lower surfaces: Close to 75D; towards the apex, close to 157D.

*Flower bracts*.—Quantity per flower: Five in a single whorl, fused; calyx, campanulate. Length: About 5 mm. Width: Less than 1 mm. Shape: Fused. Apex: Crenate. Margin: Entire. Texture, upper and lower surfaces: Smooth, glabrous. Color, upper and lower surfaces: Close to 145D.

*Receptacle bracts*.—Quantity per inflorescence: About ten in a single whorl. Length: About 1.1 cm. Width: About 2 mm. Shape: Lanceolate. Apex: Acute. Base: Broadly cuneate. Margin: Entire. Texture, upper and lower surfaces: Sparsely pubescent. Color, upper and lower surfaces: Close to 137B.

*Peduncles*.—Length: About 26.5 cm. Diameter: About 1.5 mm. Strength: Strong. Angle: Mostly erect. Texture: Sparsely pubescent. Color: Close to 138B.

*Reproductive organs*.—Androecium: Stamens per flower: Five. Filament length: About 4 mm. Filament color: Close to NN155D. Anther shape: Narrowly oblong. Anther length: About 3 mm. Anther color: Close to N155B to N155C. Pollen amount: None observed. Gynoecium: Pistils per flower: One. Pistil length: About 1 cm. Stigma shape: Club-shaped. Stigma color: Close to NN155D. Style length: About 9 mm. Style color: Close to NN155C. Ovary color: Close to 145B to 145C.

*Seed and fruit*.—Seed and fruit development have not been observed on plants of the new *Scabiosa*.

Disease/pest resistance: Under commercial production conditions, plants of the new *Scabiosa* have not been observed to be resistant to pathogens or pests common to *Scabiosa* plants.

Garden performance: Plants of the new *Scabiosa* have been shown to have good garden performance; to tolerate wind and rain, to be hardy to USDA Zone 6 and to tolerate high temperatures up to about 35° C.

It is claimed:

1. A new and distinct *Scabiosa* plant named 'Champagne' as illustrated and described.

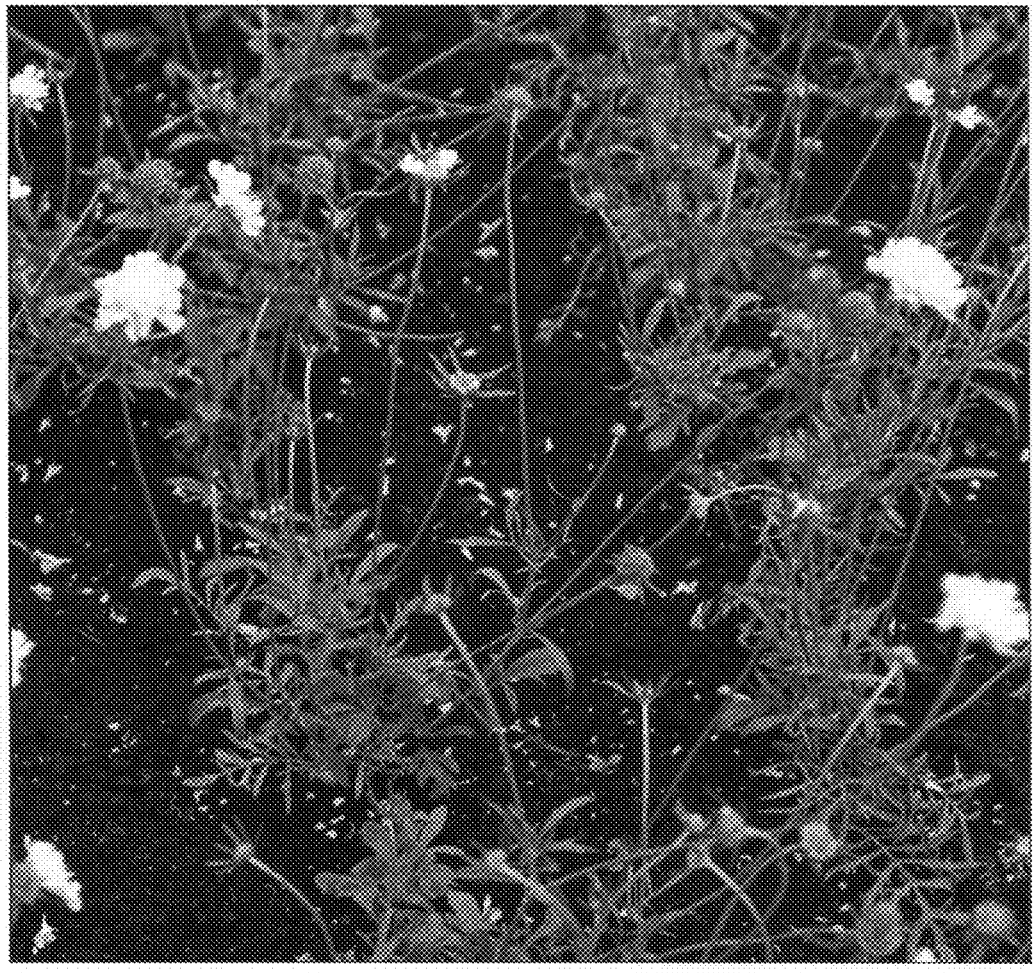
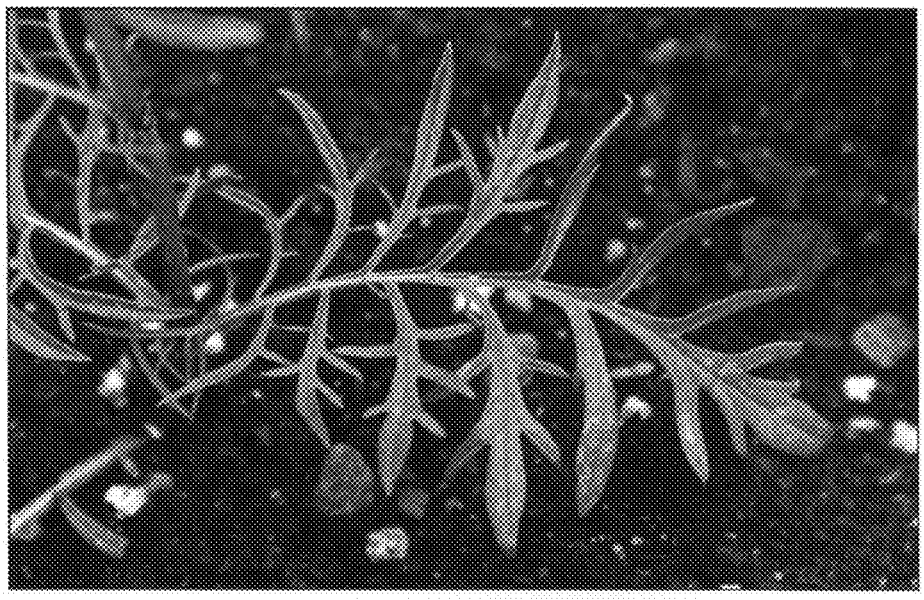

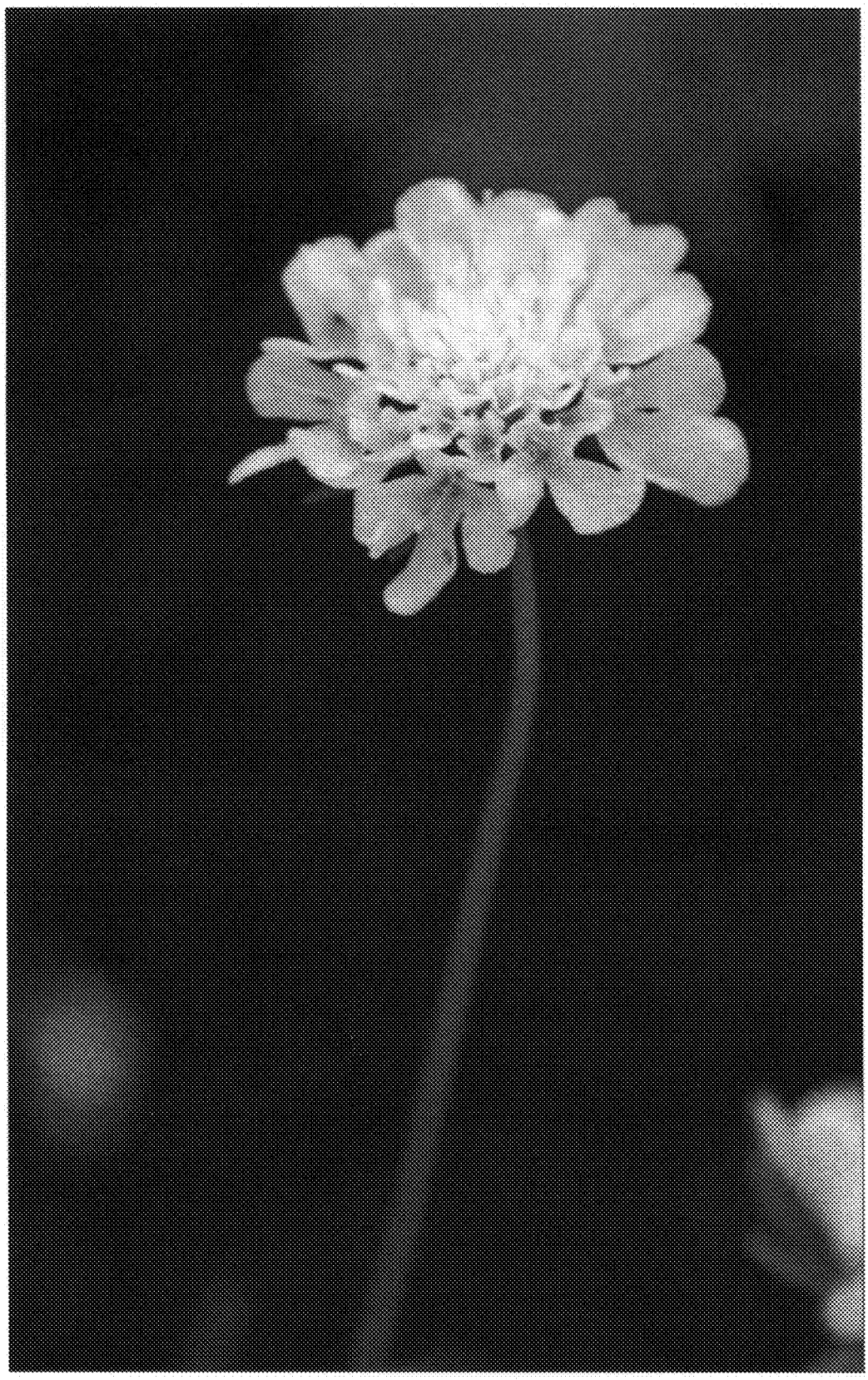

* * * * *